(12) United States Patent
Serpentino et al.

(10) Patent No.: US 6,290,655 B1
(45) Date of Patent: *Sep. 18, 2001

(54) BLOOD COLLECTION ASSEMBLY

(75) Inventors: Peter Serpentino, Sparta; Fu-chung Lin, Wayne; Hariharan Shankar, Highland Park; Theodore S. Weir, Randolph, all of NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/512,403

(22) Filed: Feb. 24, 2000

Related U.S. Application Data

(63) Continuation of application No. 09/256,170, filed on Feb. 23, 1999, now Pat. No. 6,077,235.

(51) Int. Cl.⁷ .................................................... A61B 5/00
(52) U.S. Cl. ..................... 600/573; 600/577; 604/317; 604/403; 436/18
(58) Field of Search .................................. 600/573, 576, 600/577, 580, 583; 604/265, 266, 317, 403, 415, 416; 215/321, 354, 355; 422/99, 102; 428/34.4, 34.6, 34.7, 35.9; 436/18, 63

(56) References Cited

U.S. PATENT DOCUMENTS

| | | | | |
|---|---|---|---|---|
| 4,242,474 | * | 12/1980 | Shinohara et al. | 525/404 |
| 4,397,318 | * | 8/1983 | Burns | 128/763 |
| 4,856,533 | * | 8/1989 | Anraku et al. | 128/763 |
| 4,967,763 | * | 11/1990 | Nugent et al. | 128/763 |
| 5,257,633 | * | 11/1993 | Volger et al. | 600/576 |
| 5,306,270 | * | 4/1994 | Macartney et al. | 600/573 |
| 5,419,872 | * | 5/1995 | Montgomery et al. | 422/102 |
| 5,466,749 | * | 11/1995 | Rolando et al. | 525/54.1 |
| 5,686,157 | * | 11/1997 | Harvey et al. | 428/36.7 |
| 5,763,033 | * | 6/1998 | Tropsha et al. | 600/577 |

\* cited by examiner

*Primary Examiner*—Eric F. Winakur
*Assistant Examiner*—Charles Marmor, II
(74) *Attorney, Agent, or Firm*—Richard E. Brown

(57) ABSTRACT

An assembly for collection of a blood sample includes a hydrophobic plastic tube and a non-exudable block or graft copolymer having a hydrophobic domain compatible with and interpenetrated in the matrix of the tube plastic and a hydrophilic domain which provides a hydrophilic interior wall surface to the container. The invention includes a method to make the container.

5 Claims, 10 Drawing Sheets

BLOOD COLLECTION ASSEMBLY

This application is a continuation of Ser. No. 09/256,170, filed on Feb. 23, 1999, now U.S. Pat. No. 6,077,235.

BACKGROUND OF THE INVENTION

1. Field of the Invention

This invention relates to blood collection and, more particularly, relates to a plastic blood sample collection assembly and method for its manufacture.

2. Background

Blood samples are routinely taken in glass evacuated tubes. One end of a double-ended needle is inserted into a patient's vein. The other end of the needle then punctures a septum covering the open end of the tube so that the vacuum in the tube draws the blood sample through the needle into the tube. Using this technique, a plurality of samples can be taken using a single needle puncture of the skin.

In addition, recent advancements in analytical instrumentation have made it possible to carry out a variety of hematological or chemical diagnostic procedures on very small quantities of blood, such as may be obtained by puncture of a patient's finger, earlobe or an infant's heel. Accordingly, a variety of blood sample microcollection devices have been disclosed in the art.

Plastic tubes have been proposed for blood collection. Plastic offers a number of advantages over glass such as lower breakage, less weight in shipment, and easier disposal by incineration. However, blood does not flow smoothly over hydrophobic surfaces, and blood components, such as platelets, fibrin or clotted blood generally adhere tenaciously to plastic surfaces and hang up on the walls of plastic collection tubes. This is a particular problem in small diameter gravity actuated microcollection tubes during sample collection or in vacuum tubes during subsequent centrifugation. Thus, in any collection apparatus, it is highly advantageous if the collection tube has a surface which resists adherence to blood components at any stage of the collection process or analysis procedure.

Adherence of blood components is not a problem with glass collection tubes, and accordingly, one approach to overcoming this problem in plastic has been to modify the plastic surface to be more glass-like, i.e., to present a hydrophilic surface to the blood. To this end, collection tubes have been treated with a gas plasma to alter the surface chemistry by introduction of heteroatoms. In another, the interior wall surface of the plastic tube has been modified by coating with materials such as surface active agents, water soluble polymers or water insoluble polymers carrying hydrophilic-hydrophobic copolymers.

While the above disclosures have improved blood flow and reduced adherence to plastic blood collection tubes, the problem has not been totally solved because the copolymers on the prior art surfaces are partially or completely removed by the blood so that the surfaces revert back to hydrophobic. There is a need for a collection tube in which adherence is avoided until analysis is complete, and no foreign materials are introduced into the plasma, serum or clot which may interfere with subsequent blood analysis.

SUMMARY OF THE INVENTION

An assembly for blood sample collection comprises a hydrophobic plastic tube which does not undergo any structural deformation when heated above its glass transition temperature and is thus capable of sealingly engaging a closure for an open end of the tube. The assembly includes a block or graft copolymer having a hydrophilic domain and a hydrophobic domain compatible with and interpenetrated into the tube polymer. In this disclosure, the term domain includes the total hydrophobic or hydrophilic segments present in the copolymer. The term compatible, as known in the art, refers to polymers which contain identical or similar functional moieties which blend together into a single polymeric phase when heated. The term interpenetrated is used to describe compatible polymeric domains which are intimately mixed throughout at least a portion of an article's cross-section so that they form a substantially single polymeric phase. It is believed, although not proven, that the long polymer molecules become entangled to form this phase whereas non-compatible domains do not entangle. Preferred assemblies are polyester evacuated collection tubes with puncturable closure or polypropylene microtubes having a cap and an integral lip.

The interpenetration of the hydrophobic domain in the tube polymer prevents exudation of the copolymer into a blood sample, and the block or graft nature of the copolymer allows at least a portion of the hydrophilic domain to extend to the interior wall surface of the tube and provide hydrophilicity thereto.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having a closed end and an open end such as, for example, bottles, vials, flasks and the like, preferably tubes. The invention will henceforth be described in terms of the preferred tube with the understanding that the disclosure herein may equally well be applied to other containers. It is also understood that, while the invention is herein disclosed in terms of the preferred blood collection tube, the collection tube may equally well be used for collection of any other body fluid.

While the tube may be dimensioned to take a blood sample of any volume, preferred tubes are standard size as known in the art. Thus the tube may be a gravity actuated microcollection tube of conventional size, generally 40–50 mm long and 5–10 mm in internal diameter. On the other hand, vacuum actuated containers designed for larger samples are generally 50 to 150 mm long and 10–20 mm in diameter. Representative conventional microcollection tubes are fully described in U.S. Pat. Nos. 4,967,763 and 5,288,466, and conventional vacuum blood collection tubes are disclosed in U.S. Pat. Nos. 4,985,026 and 4,856,533.

The drawings illustrate a vacuum blood collection tube with stopper and a gravity actuated microcollection tube with mating lip with no intention of limiting the invention to the designs shown. As is fully appreciated by one skilled in the art, the design of the collection tube and stopper is not critical, and hydrophilicity to prevent adhesion of blood components, clot and fibrin may be imparted to tubes of any design.

Figure 1:
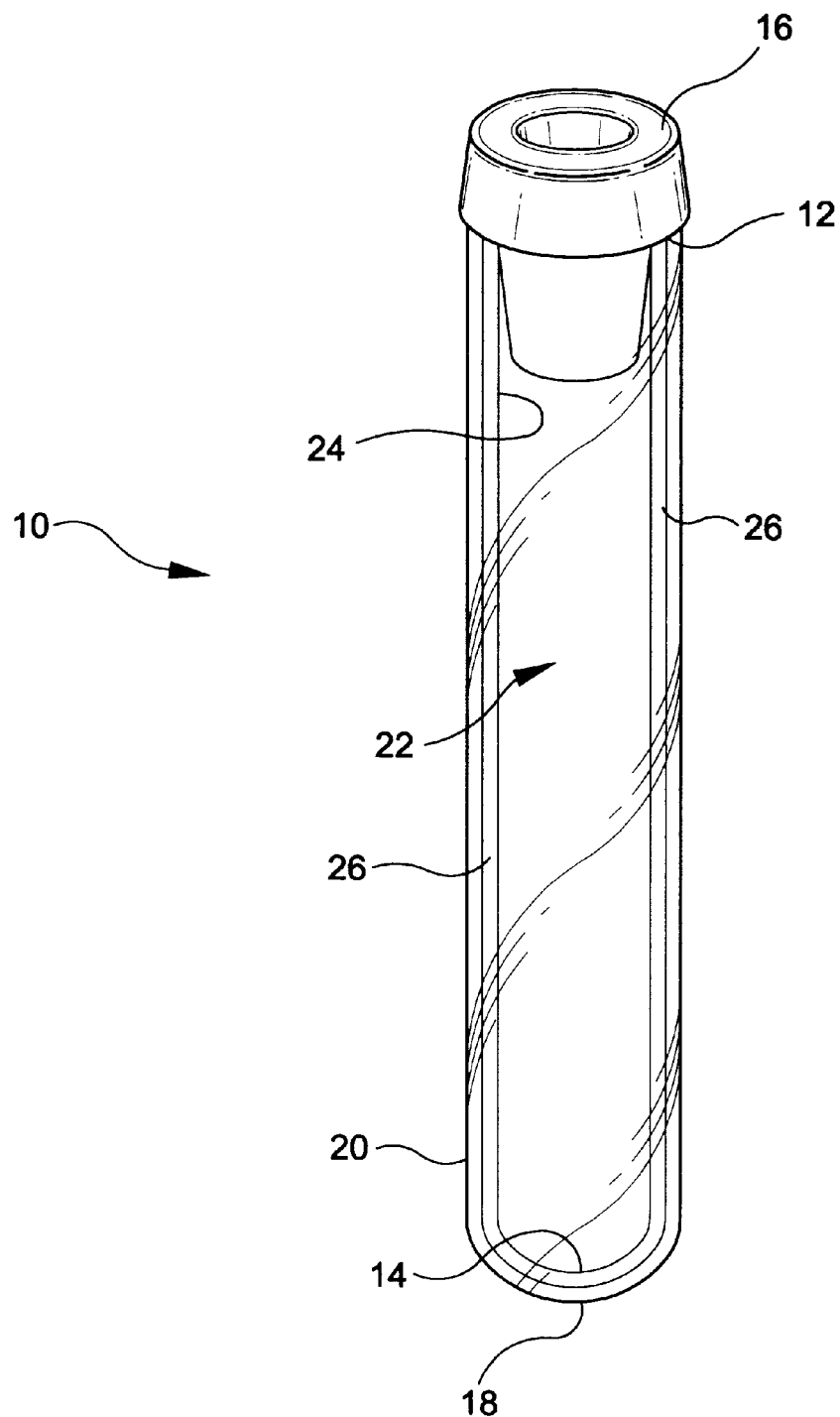
FIG. 1 is a perspective view of a typical blood collection tube with puncturable stopper.
Figure 3:
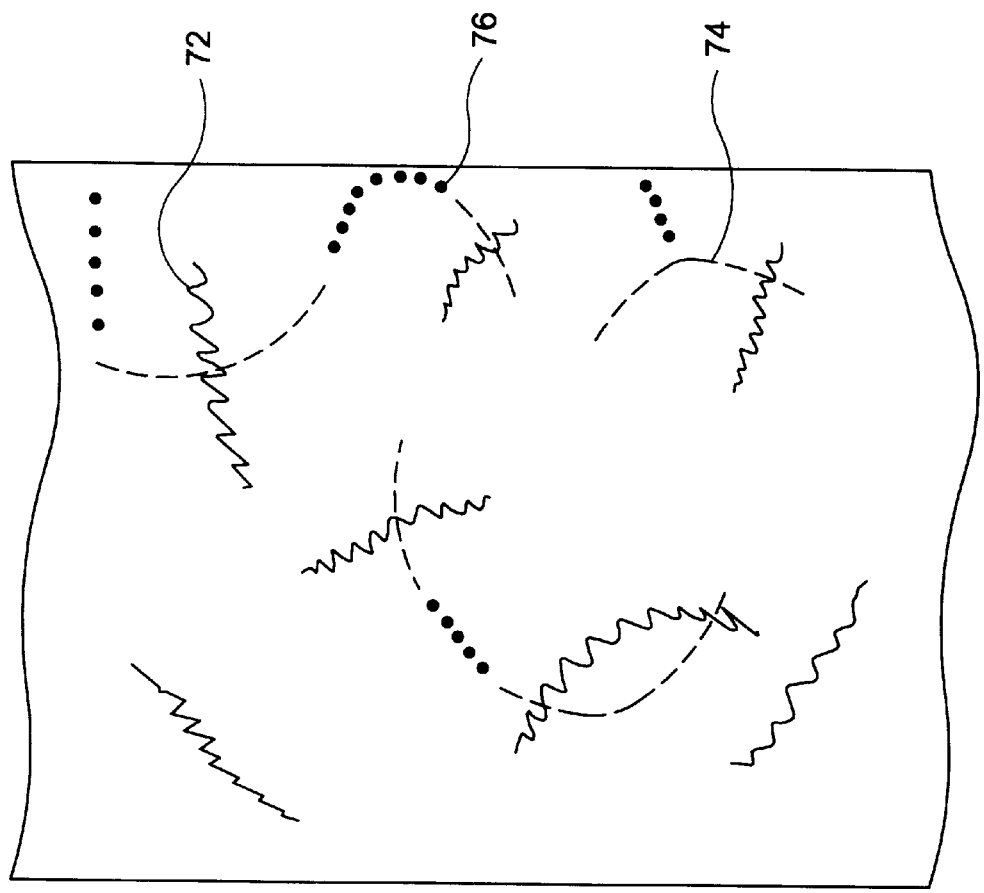
FIG. 3 is a schematic representation of the molecular orientation of the polymer molecules in the tube of the invention.

FIG. 1 illustrates a blood collection tube 10 of the invention having an open end 12, a closed end 14 and a stopper 16 in open end 12. Tube 10 has a bottom wall 18 and a sidewall 20 which, together with stopper 16, enclose an interior volume 22 of the tube which preferably is evacuated. Stopper 16 is preferably puncturable and extends into and presses against the inside wall surface 24 of sidewall 20 to maintain stopper 16 in place. Copolymer 26, is interpenetrated (as illustrated in FIG. 3) in at least a portion of sidewall 20 and bottom wall 18. Puncturable stoppers for evacuated sample collection tubes are standard in the art and may be made of any suitable material, such as KRATON™ (trademark of Shell Corp for styrene-butadiene copolymer).

Figure 2:
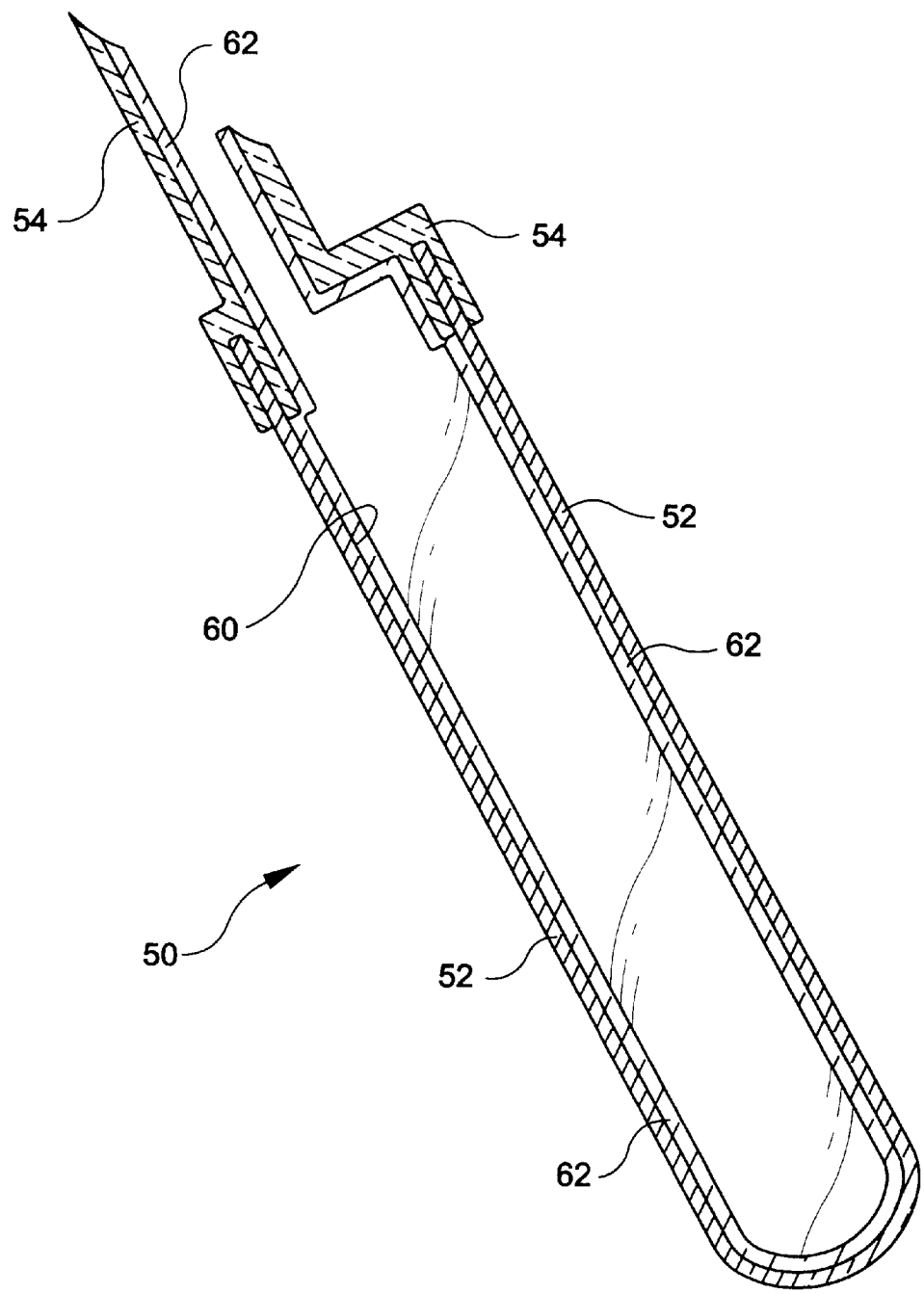
FIG. 2 is a longitudinal sectional view of a typical blood microcollection tube with mating lip portion.

FIG. 2 illustrates a typical microcollection assembly 50 including collection tube 52 and lip 54 to aid in directing a blood sample from a lance wound into the tube. While the drawing shows the tube and lip to be separate, they may equally well be a single integral unit consequent to the molding process and be configured to mate in sealing engagement with a closure or cap (not shown) after sample taking. Inside wall 60 of tube 52, and preferably lip 54, have thereon the copolymer 62 of the invention. While the drawing shows the copolymer as a coating, in actuality, the hydrophobic domain is interpenetrated in at least a portion of tube 52 so that the hydrophilic domain is exposed at the surface of the tube. This situation is illustrated in FIG. 3, wherein tube wall segment 70 has polymer molecules 72 interpenetrated with blocks 74 of the copolymer hydrophobic domain so that the tube polymer and the hydrophobic domain are in effect a single polymeric phase. At least a portion of the blocks or grafts of copolymer hydrophilic domain 76 extends to the wall of the tube to confer hydrophilicity.

Any thermoplastic polymer or copolymer which is compatible with the hydrophobic domain of the copolymer may be used for the container. Suitable tube polymers are, for example, polyolefins such as polyethylene and polypropylene (PP), polyesters such as polyethylene terephthalate (PET), polystyrene, polyvinylchloride and polyacrylic. PP is preferred for microcollection tubes and PET is preferred for vacuum collection tubes.

The copolymer having a generally hydrophobic domain and a generally hydrophilic domain may be a block or graft copolymer. The monomers for the copolymer domains must be copolymerizable with each other such as by conventional addition or condensation polymerization, and the hydrophobic copolymer domain must be compatible with the tube polymer. For a polypropylene tube, the hydrophobic domain of the copolymer may have, for example, a hydrocarbon moiety for compatibility, such as polyethylene, polypropylene and other polyolefins, polystyrene, polyacrylonitrile and the like. For a PET tube, the hydrophobic domain of the copolymer may have, for example, a carbonyl group or an aromatic ring for compatibility. Thus, suitable hydrophobic copolymer domains may be present in other polyesters, polyamides, polyacrylates polyvinylacetate (PVAC) and the like. Suitable hydrophilic moieties may be provided by polyalkyleneoxides, such as polyethyleneoxide (PEO) polyvinyl alcohol, polyvinyl pyrrolidone, polyhydroxyalkyl acrylates, polystyrene sulfonate and the like. A preferred copolymer for a PET tube is a copolymer of PET and PEO, and a preferred copolymer for a PP tube is a copolymer of polyethylene and PEO. Choice of suitable monomers to achieve a copolymer having a hydrophilic domain and a hydrophobic domain compatible with the tube polymer is well within the purview of one skilled in the polymer arts, and no further details regarding this aspect of the invention is needed for a full understanding by one skilled in the art.

As mentioned above, the compatibility of the tube polymer and the hydrophobic domain provides a substantially single polymeric phase. In accordance with the invention, it has been found that this single phase precludes or greatly retards exudation of the copolymer from the tube polymer so that at least a portion of the hydrophilic domain is present at the inside wall surface of the tube to provide prolonged hydrophilicity.

In the copolymer, the hydrophilic domain may be from about 10 to 90, preferably about 30 to 70 weight percent. The copolymer may be about 20 to 80, preferably about 30 to 70 weight percent of the total polymer in the tube.

The blood collection tube of the invention may be prepared by compounding the tube polymer with the copolymer by any conventional method prior to injection molding. In the preferred procedure, the copolymer may be coated by any conventional method such as spraying, dipping or filling and aspirating onto the inside wall surface of the tube, and the coated tube is then heated to a temperature up to and preferably above the glass transition temperature of the tube polymer whereby the hydrophobic domain of the copolymer interpenetrates into the tube polymer to form a single polymeric phase. A suitable temperature for heating to effect interpenetration and avoiding any structural deformation of the tube is easily determined by one skilled in the polymer arts.

Any additive useful in blood analysis, including both procoagulants and anticoagulants, may be present in the tube. In this way, the assembly, by proper selection of additive, may be used across the entire spectrum of commercial blood collection tubes. Thus, if analysis is to be performed on serum, a procoagulant maybe used to enhance the rate of clotting. A representative, but not exhaustive list of suitable procoagulants are particulate clot activators such as silica particles and enzyme clot activators, such as elagic acid, fibrinogen and thrombin. If plasma is needed for analysis, an anticoagulant is generally provided to inhibit coagulation during centrifugation. Suitable anticoagulants are chelators such as oxalates, citrates, and EDTA or enzymes such as heparin.

The tube may contain a conventional thixotropic gel which, on centrifugation, migrates to the interface between the serum and the cells and serves for separation of the layers.

The vacuum blood collection tube of the invention may also be treated by any conventional methodology to enhance its resistance to the passage of moisture or gas which would reduce the tube vacuum and affect the blood draw volume. While not wishing to be limited thereby, one commonly used procedure for conferring gas and moisture impermeability is to apply a coating of a siliceous material, such as SiOx, to the outside of the tube.

Experimental

EXAMPLE 1

Invention

A. Standard PET blood collection tubes were filled with an aqueous solution of a PET-PEO block copolymer and held at 60° C. for 1 minute. Ten tubes each were thus treated with 0.5, 1.0, and 5.0% by wt. solutions. All tubes were decanted, aspirated to dry, then heated for 20 sec. in an oven preheated to 130° C. The tubes thus prepared were tested for copolymer exudation in accordance with Example 4. The results are given in the Table.

B. The procedure of A was repeated using a copolymer of vinyl alcohol and vinyl acetate (PVA-PVAc).

EXAMPLES 2A and 2B

Comparative

Tubes of the same tube polymer and copolymer as those of examples 1A and 1B were prepared by spray application of the copolymer and removal of solvent at 60° C. with an air gun. These tubes were tested as in Example 4 and the copolymers were found to exude. The results are given in the Table.

EXAMPLE 3

Invention

In the same way as in Example 1, a PP microcollection tube is treated with a copolymer of polyethylene and PEO and is found to have a nonexudably hydrophilic interior wall surface.

EXAMPLE 4

Determination of Exudability

Tubes (16×100 ml) coated in accordance with examples 1A and 1B (10 tubes from each group) and 10 uncoated control tubes were charged with 3 ml of deionized water and rotated at room temperature for 24 hours. The contents of the tubes were poured into clean empty tubes and the water evaporated from each. The tubes were dried thoroughly, and 250 ul of acetone added to dissolve any coating which was removed by the water. The acetone was deposited onto a barium fluoride crystal, the acetone evaporated and the residual sample on the crystal subjected to FTIR analysis using a Nicolet 20SXC instrument. IR transmittance for each extracted sample was compared with the control. A tube coating was judged non-exudable if the transmittance was about the same as the control. The presence of exudability was indicated by the presence of IR peaks corresponding to those of a control IR curve of the copolymer.

TABLE

| Experiment | Conc. | Exudability |
|---|---|---|
| Example 1A | 0.5 | (−) |
| 1.0 | | (−) |
| 5.0 | | (−) |
| Example 1B | 0.5 | (−) |
| 1.0 | | (−) |
| 5.0 | | (−) |
| Example 2A | 0.5 | + |
| 1.0 | | + |
| 5.0 | | + |
| Example 2B | 0.5 | + |
| 1.0 | | + |
| 5.0 | | + |

It is seen from the Table that, when PET blood collection tubes are treated in accordance with the process of the invention (Example 1), the copolymer is non-exudable after 24 hour contact with water. In contrast, tubes treated in accordance with the prior art (Example 2) are seen to exude the copolymer when tested under the same conditions.

Figure 4:
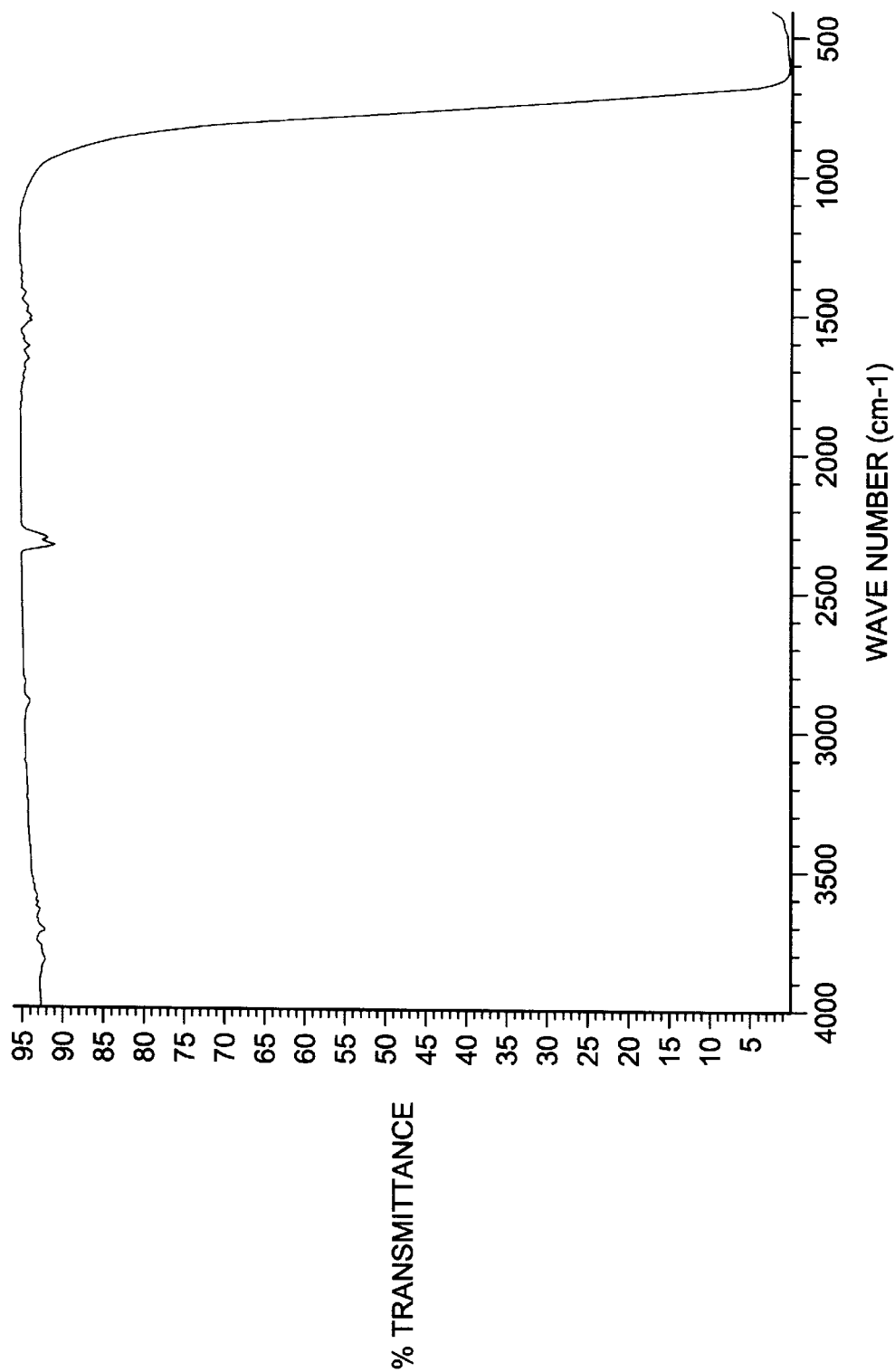
FIGS. 4–10 are infrared curves showing non-exudability for tubes of the invention and exudability for prior art tubes.
Figure 5:
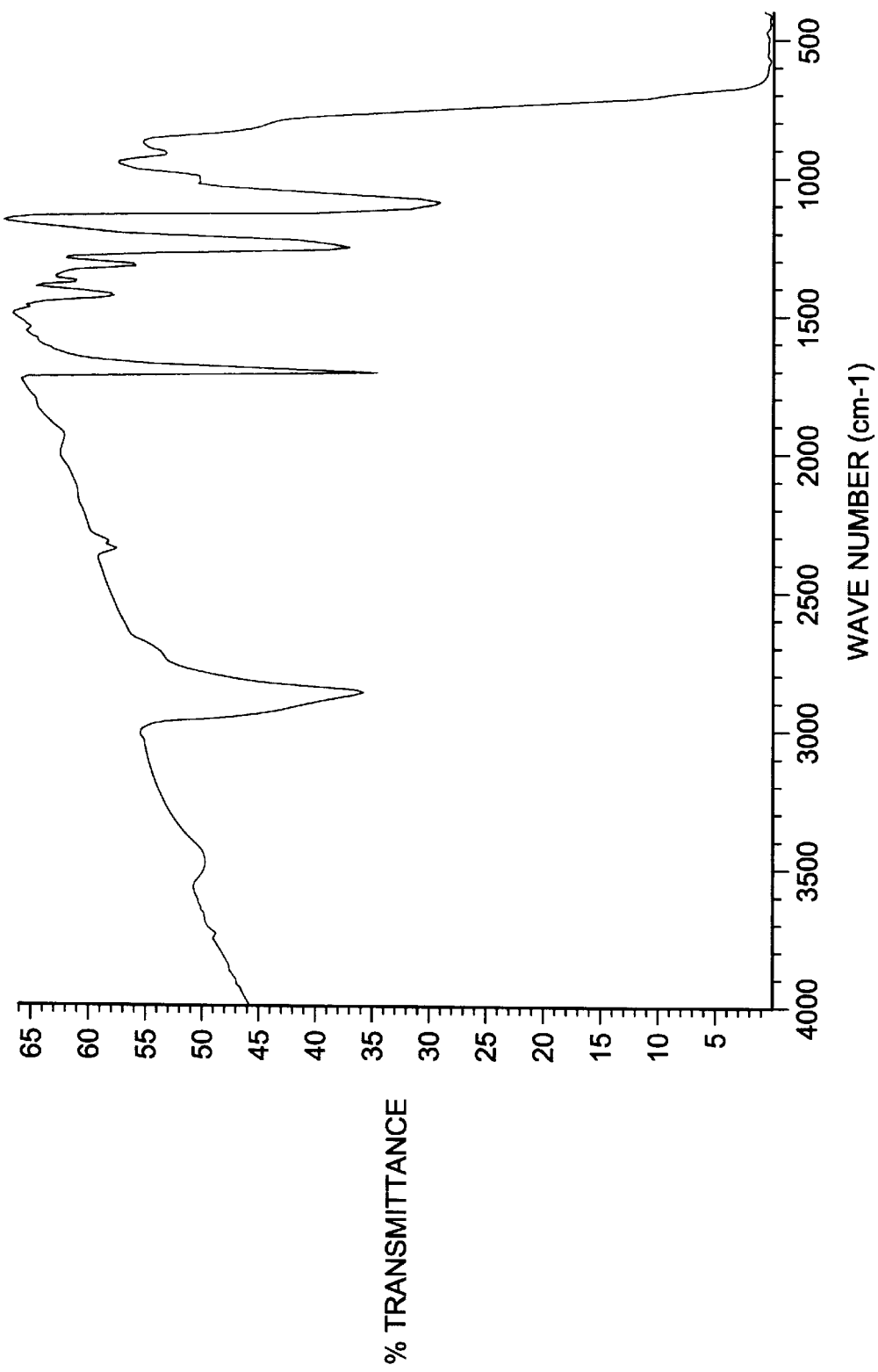
Figure 6:
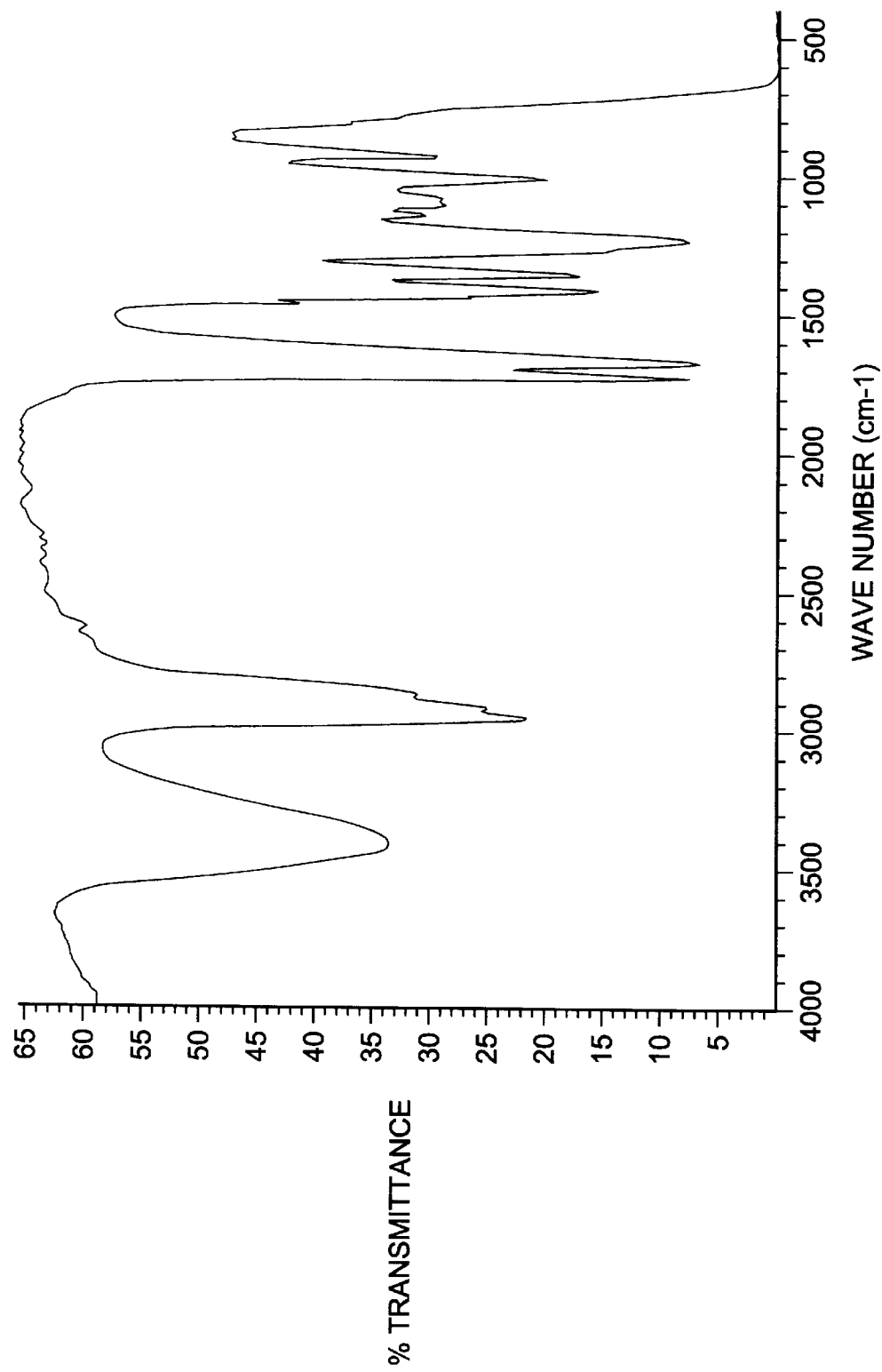
Figure 7:
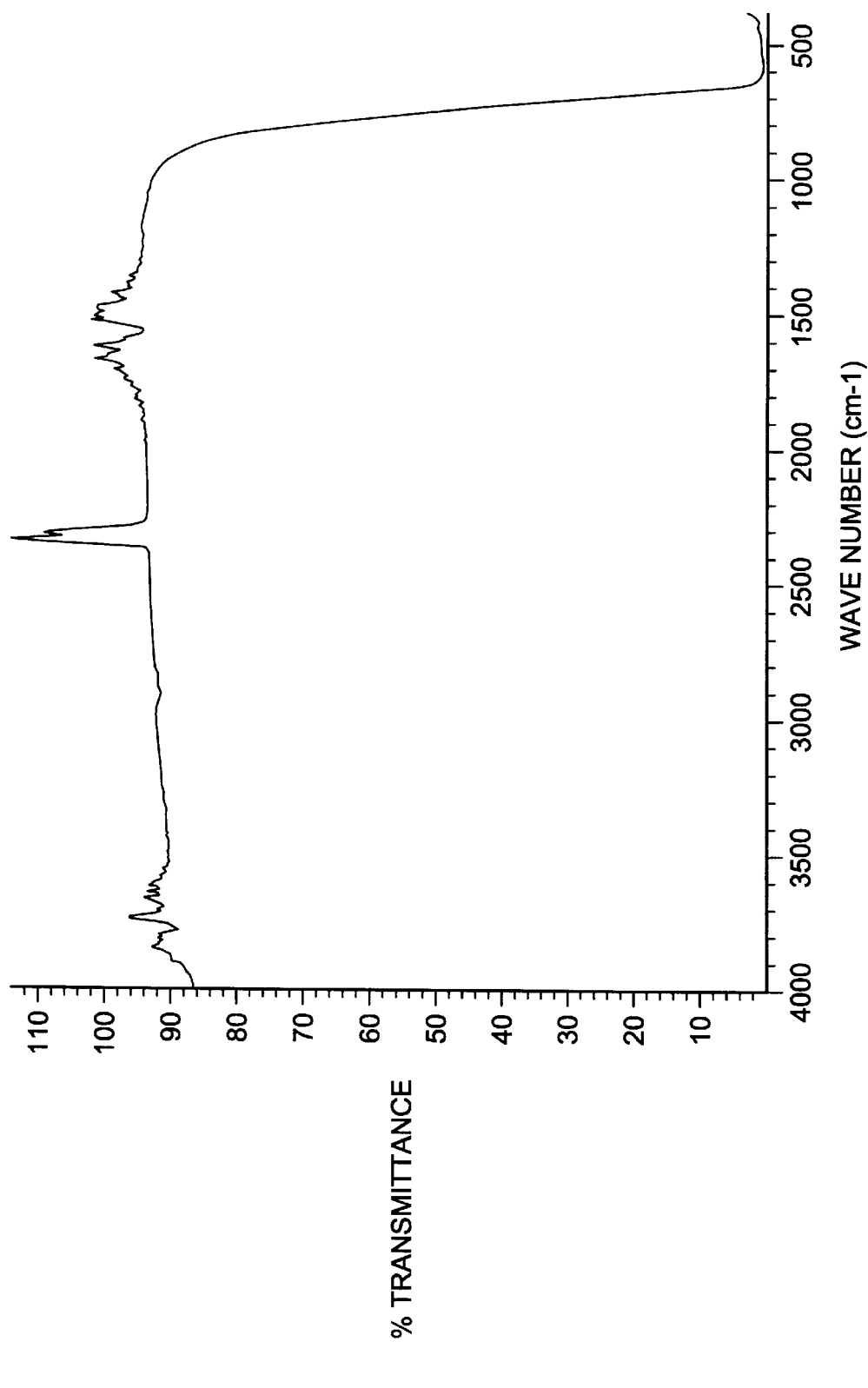
Figure 8:
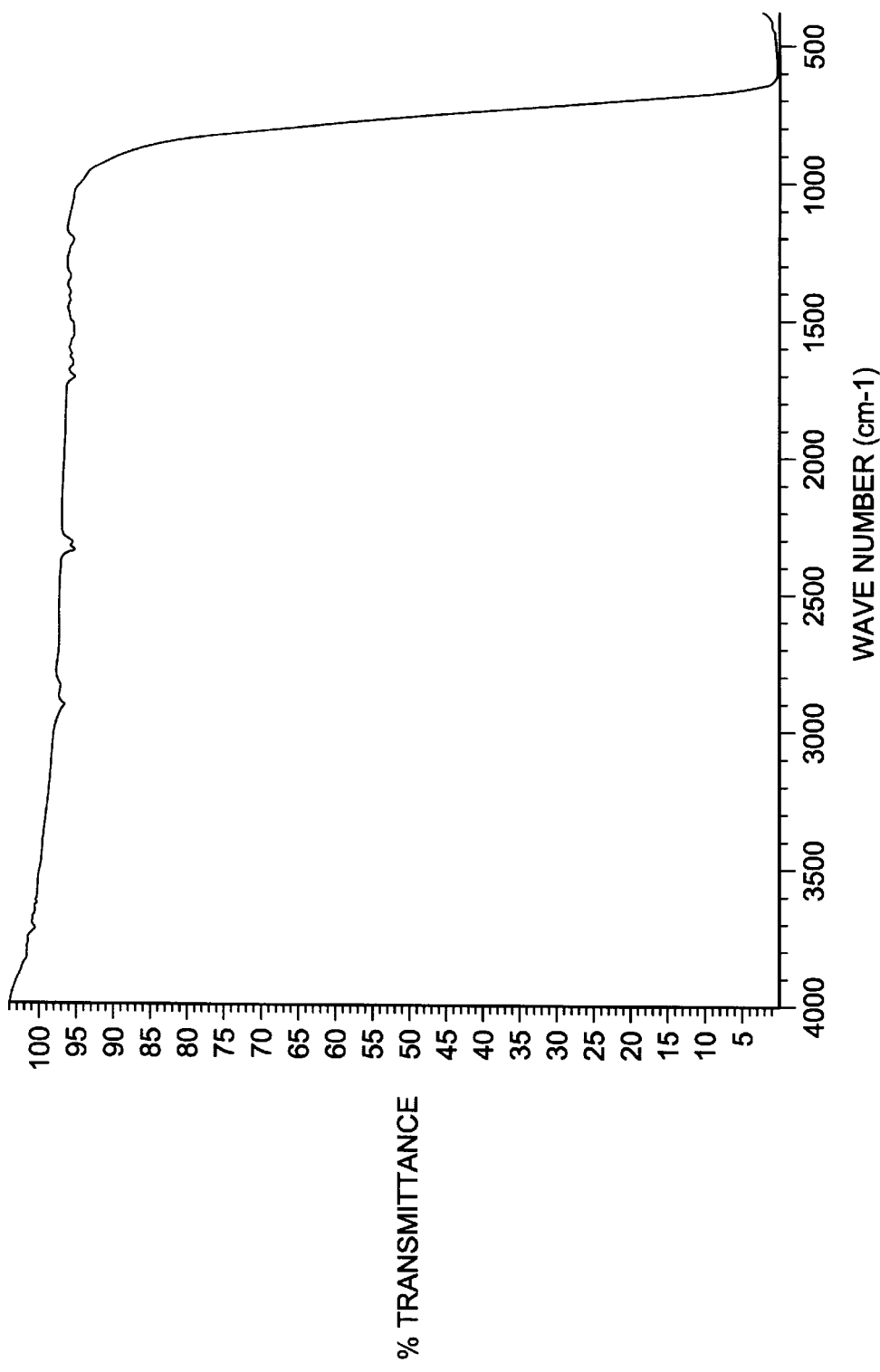
Figure 9:
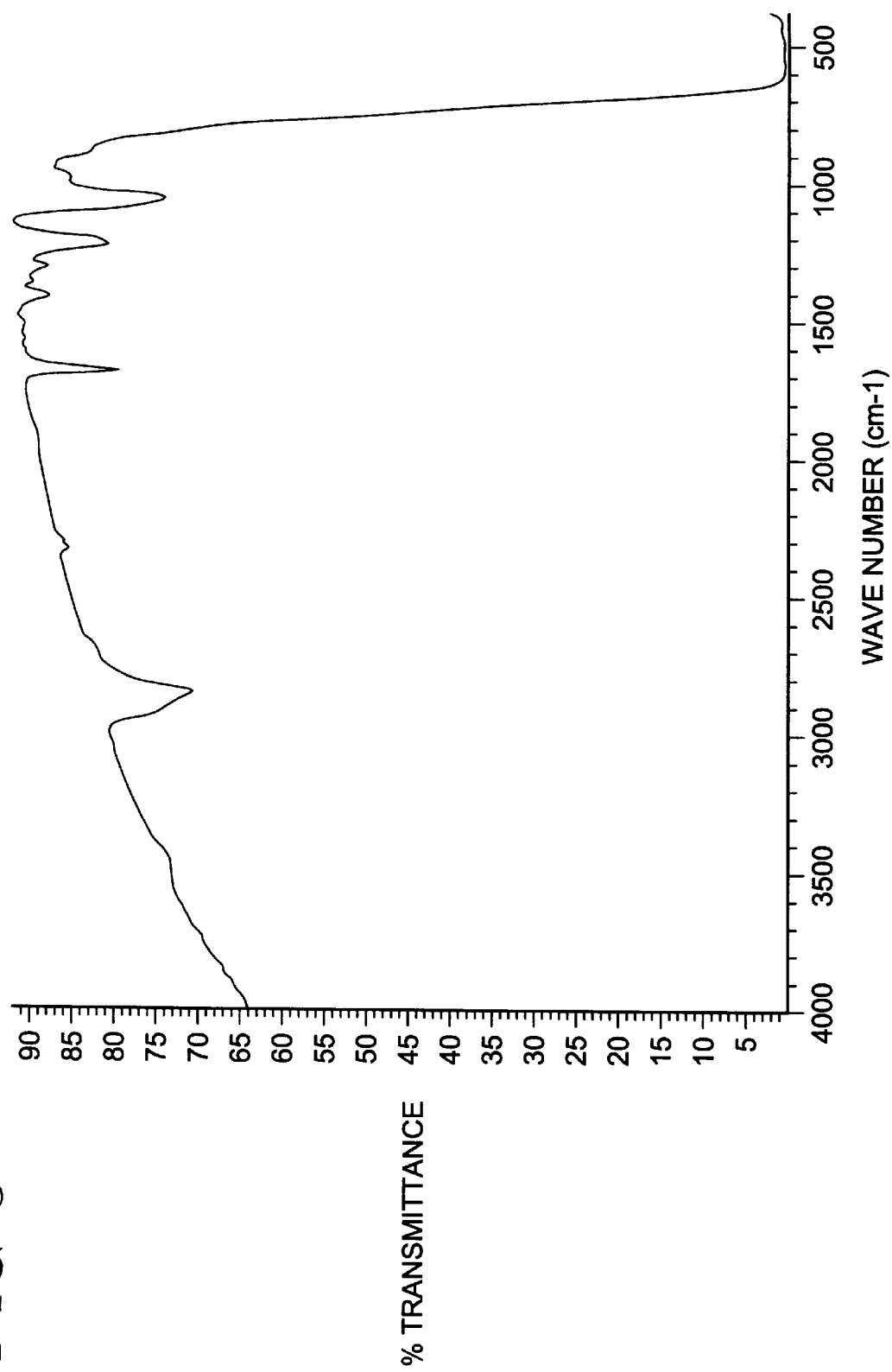
Figure 10:
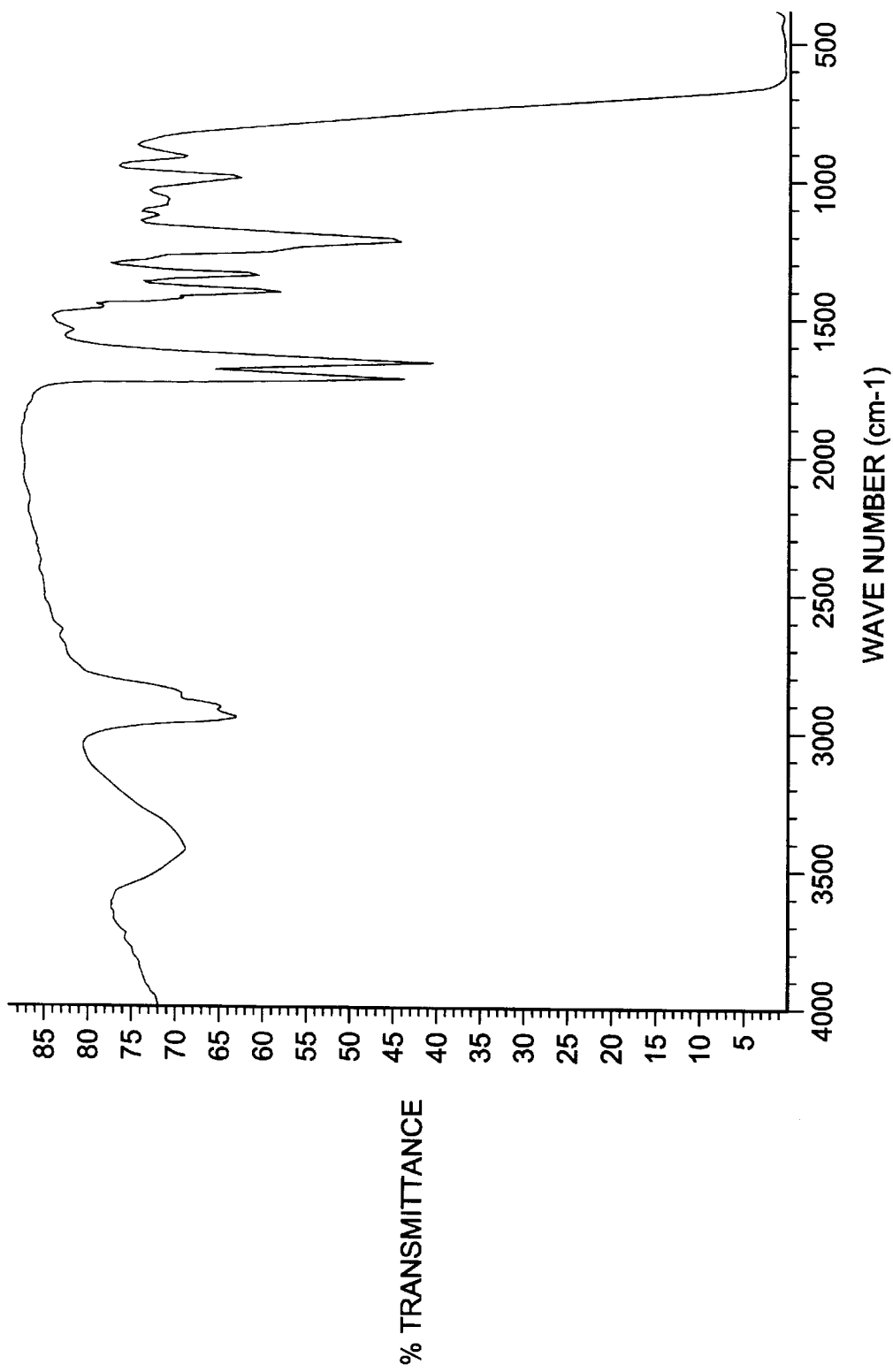

FIGS. 4, 5 and 6 are control IR curves of water, PET-PEO copolymer and PVA-PVAc copolymer respectively. FIGS. 7 and 8 are IR curves of the residues from extraction of the tubes of Example 1A and 1B according to Example 4 showing, by comparison with FIG. 4, no copolymer exudation. FIGS. 9 and 10 are IR curves of extracts of tubes made by comparative Examples 2A and 2B. These curves, by comparison with control curves (FIGS. 5 and 6) show that copolymer exudation has occurred.

What is claimed is:

1. A sample assembly comprising:
   a) a plastic hydrophobic blood collection tube having a closed end and an open end for receiving a patient's body fluid sample; and
   b) a block or graft copolymer having a hydrophilic domain and a hydrophobic domain non-exudably interpenetrated in the wall of said tube, said hydrophilic domain providing hydrophilicity to the interior wall surface of said tube, said hydrophobic domain being compatible with and forming a single polymeric phase with the plastic of the tube.

2. The assembly of claim 1 further comprising an additive in said tube.

3. The assembly of claim 1 wherein said tube further comprises a puncturable closure in said open end and said tube is evacuated.

4. The assembly of claim 3 further comprising a coating on said tube for conferring gas and moisture impermeability.

5. The assembly of claim 1 wherein said tube is a gravity actuated microcontainer further comprising a lip portion for sample collection by engagement with a lance wound.

* * * * *